(12) United States Patent
Chinta et al.

(10) Patent No.: US 8,981,109 B2
(45) Date of Patent: Mar. 17, 2015

(54) PROCESS FOR THE PREPARATION OF VALSARTAN

(75) Inventors: Raveendra Reddy Chinta, Hyderabad (IN); Gangadhara Bhima Shankar Nangi, Hyderabad (IN); Mahendar Reddy Nayini, Hyderabad (IN); Somappa Somannavar Yallapa, Hyderabad (IN); Shankar Reddy Budidet, Hyderabad (IN); Islam Aminul, Hyderabad (IN); Sivakumaran Meenakshisunderam, Hyderabad (IN)

(73) Assignee: Aurobindo Pharma Ltd, Hyderabad (IN)

( * ) Notice: Subject to any disclaimer, the term of this patent is extended or adjusted under 35 U.S.C. 154(b) by 58 days.

(21) Appl. No.: 13/261,552

(22) PCT Filed: Jun. 24, 2011

(86) PCT No.: PCT/IB2011/001483
§ 371 (c)(1),
(2), (4) Date: Dec. 21, 2012

(87) PCT Pub. No.: WO2012/001484
PCT Pub. Date: Jan. 5, 2012

(65) Prior Publication Data
US 2013/0144067 A1    Jun. 6, 2013

(30) Foreign Application Priority Data
Jul. 2, 2010 (IN) .......................... 1866/CHE/2010

(51) Int. Cl.
*C07D 257/04* (2006.01)

(52) U.S. Cl.
CPC .................................. *C07D 257/04* (2013.01)
USPC ....................................................... 548/253

(58) Field of Classification Search
None
See application file for complete search history.

(56) References Cited

FOREIGN PATENT DOCUMENTS

WO    WO 2009/125416    * 10/2009    ............ C07C 253/30

* cited by examiner

*Primary Examiner* — Alicia L Otton
(74) *Attorney, Agent, or Firm* — Jay R Akhave

(57) ABSTRACT

The present invention relates to a process for the preparation of pure Valsartan (I) substantially free from impurities of formulae (Ia), (Ib), and (Ic), which comprises: (i) condensing 2-(4'-bromomethylphenyl)benzonitrile of formula (II) with L-valine methyl ester hydrochloride of formula (V) in the presence of a base in a solvent to produce N-[(2'-cyanobiphenyl-4-yl)methyl]-(L)-valine methyl ester of formula (VI); (ii) treating the compound VI of step (i) with acid followed by treating with base to produce pure compound VI substantially free from dimeric impurity of formula (Via); (iii) reacting the pure compound of formula (VI) with n-valeryl chloride in the presence of a base to produce pure N-valeryl-N-[(2'-cyano-biphenyl-4-yl)methyl]-(L)-valine methyl ester (VII) substantially free from alkene impurity of formula (Vila); (iv) reacting the compound of formula (VII) with trialkyltin chloride and a metal azide in a solvent at a reflux temperature to produce N-(1-oxopentyl)-N-[[2'-(2-tributyltintetrazol-5-yl)-(1,1'-biphenyl)-4-yl]methyl]-(L)-valine methyl ester of formula (VHIb) free from thermal degradation impurity (Villa); (v) hydrolyzing the compound of formula (VHIb) in the presence of alkaline conditions to produce Valsartan (I).

13 Claims, No Drawings

PROCESS FOR THE PREPARATION OF VALSARTAN

FIELD OF THE INVENTION

The present invention relates to an improved process for the preparation of Valsartan of formula I.

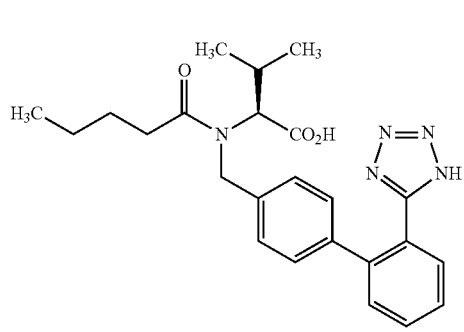

Formula I

BACKGROUND OF THE INVENTION

Valsartan is chemically known as N-(1-oxopentyl)-N-[[2'-(1H-tetrazol-5-yl)[1,1'-biphenyl]-4-yl]methyl]-L-valine. Valsartan is a non-peptide $AT_1$-subtype angiotensin II receptor antagonist. Angiotensin II is formed from angiotensin I in a reaction catalyzed by angiotensin-converting enzyme (ACE kininase II). Angiotensin II is the principal pressor agent of the renin-angiotensin system, with effects that include vasoconstriction, stimulation of synthesis and release of aldosterone, cardiac stimulation, and renal reabsorption of sodium. Valsartan blocks the vasoconstrictor and aldosterone-secreting effects of angiotensin II by selectively blocking the binding of angiotensin II to the $AT_1$ receptor in many tissues, such as vascular smooth muscle and the adrenal gland. Its action is therefore independent of the pathways for angiotensin II synthesis. Valsartan is used for the treatment of hypertension and is marketed as the free acid under the brand name DIOVAN®.

Valsartan and its pharmaceutically acceptable salts are disclosed in U.S. Pat. No. 5,399,578.

According to U.S. Pat. No. 5,399,578, the process for the preparation of Valsartan (I) involves the reaction of 4'-bromomethyl-2-cyanobiphenyl (II) with sodium acetate and glacial acetic acid to produce 2'-cyano-4-hydroxymethylbiphenyl (III), which is reacted with oxalyl chloride in dichloromethane and dimethyl sulfoxide to produce 2'-cyano-4-formylbiphenyl (IV), which is further reacted with (L)-valine methyl ester hydrochloride (V) and sodium cyanoborohydride to produce N-[(2'-cyanobiphenyl-4-yl)methyl]-(L)-valine methyl ester (VI), followed by treatment with valeryl chloride to produce N-valeryl-N-[(2'-cyanobiphenyl-4-yl)methyl]-(L)-valine methyl ester (VII), which is treated with tri-n-butyltin azide followed by flash chromatography to produce Valsartan of formula (I).

The process is as shown in Scheme-I below:

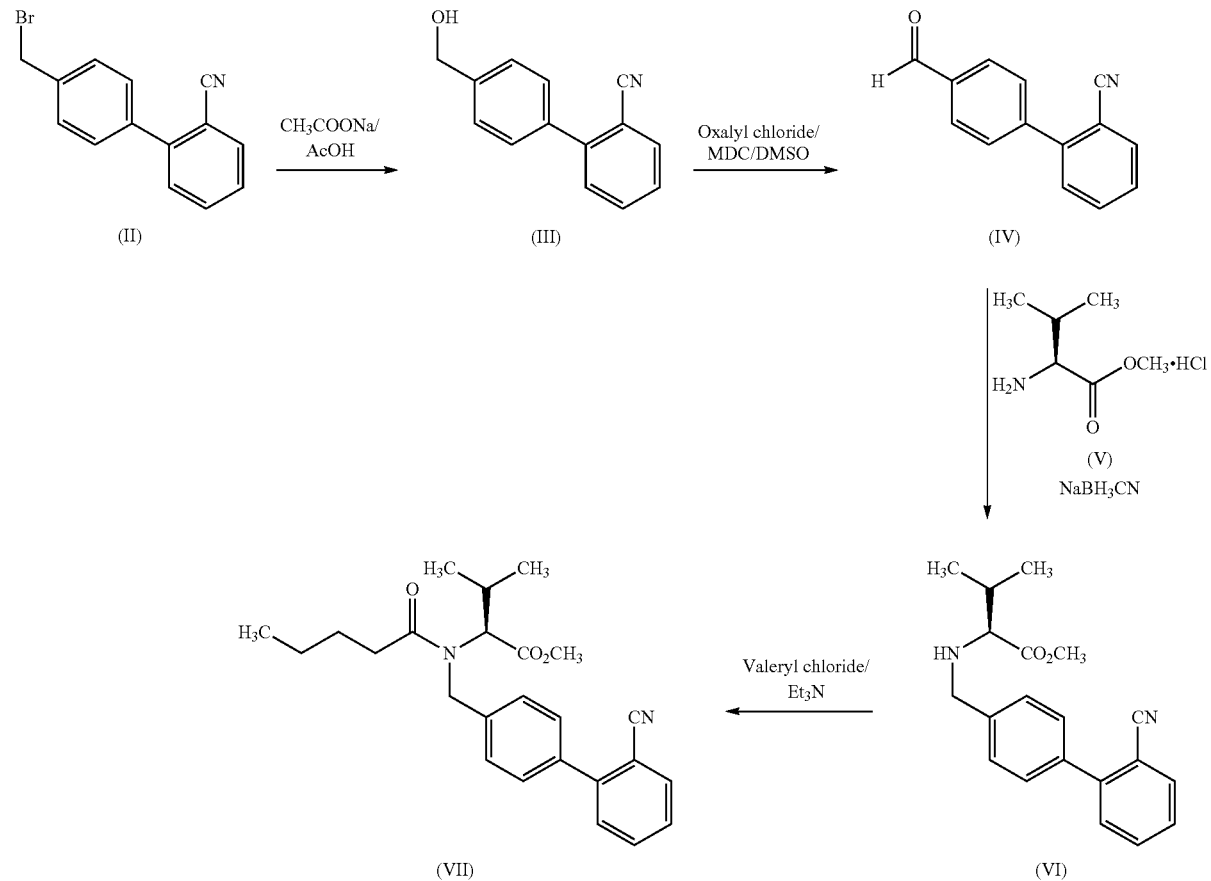

Scheme-I

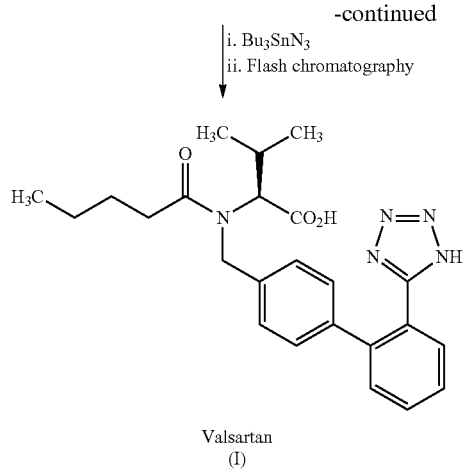

Valsartan
(I)

The major disadvantage with the above process is the use of triethylamine in the process for the preparation of the compound of formula (VII), in which process, the reaction is incomplete due to the presence of moisture, affecting the quality of the product, leading to a lower yield and requires flash chromatography for purification. Conversion of the compound of formula (VII) to Valsartan also involves flash chromatography. Employing column chromatography technique is tedious and laborious and also involves use of large quantities of solvents, and hence is not suitable for industrial scale operations.

Bioorganic & Medicinal Chemistry Letters (1994), 4(1), 29-34, reported a process for the preparation of Valsartan by reacting 4'-bromomethyl-2-cyanobiphenyl (II) with (L)-valine methyl ester hydrochloride (V) in the presence of diisopropylethylamine in methylenechloride to produce N-[(2'-cyanobiphenyl-4-yl)methyl]-(L)-valine methyl ester (VI), followed by reacting with valeryl chloride in the presence of diisopropylethylamine in methylenechloride to produce N-valeryl-N-[(2'-cyanobiphenyl-4-yl)methyl]-(L)-valine methyl ester (VII), which is further reacted with tributyltin azide in xylene to produce N-[[2'-(1H-tetrazol-5-yl)biphenyl-4-yl]methyl]-N-valeryl-(L)-valine methyl ester (VIII), followed by hydrolysis with aqueous base to produce Valsartan of formula (I).

The process is as shown in Scheme-II below:

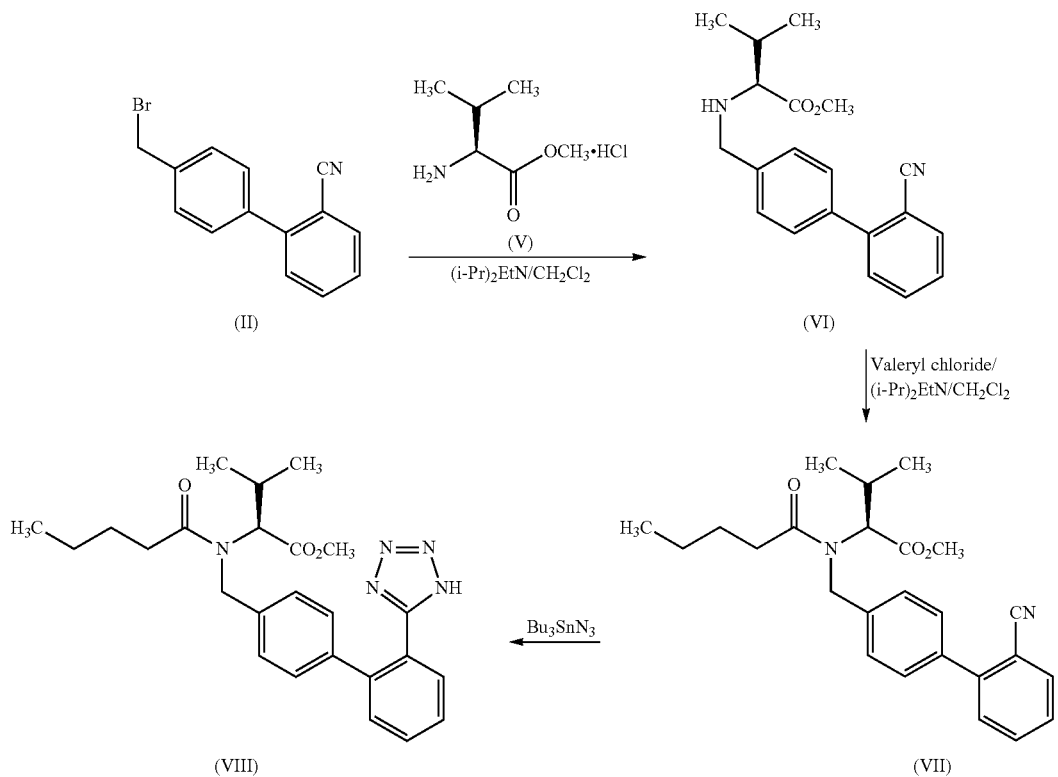

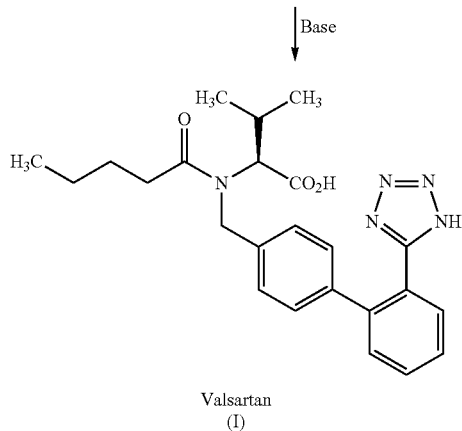

Valsartan
(I)

According to the process reported in IP. Com Journal (2006), 6(7B), 23, No. IPCOM000138267D, N-valeryl-N-[(2'-cyanobiphenyl-4-yl)methyl]-(L)-valine methyl ester (VII) is produced by condensing N-[(2'-cyanobiphenyl-4-yl)methyl]-(L)-valine methyl ester (VI) with valeryl chloride in the presence of potassium carbonate in xylene.

U.S. Pat. No. 7,659,406 B2 discloses a process for the condensation of N-[(2'-cyanobiphenyl-4-yl)methyl]-(L)-valine methyl ester (VI) or a salt thereof, with valeryl chloride in the presence of an inorganic base in a solvent to produce N-valeryl-N-[(2'-cyanobiphenyl-4-yl)methyl]-(L)-valine methyl ester (VII).

The above processes involve the condensation of halomethylbiphenyl derivative with L-valine ester is one of the important steps for the synthesis of Valsartan. It was observed that the condensation of compound of formula (II) with L-valine ester of formula (V) generates about 5% unwanted dimeric impurity of formula (VIa) along with desired compound of formula (VI). This impurity in turn is carried forward in subsequent reaction steps and results in Valsartan (I) with the undesired impurity of formula (Ia) This results in the poor yield and quality of the Valsartan product and requires additional purification step.

Formula VIa

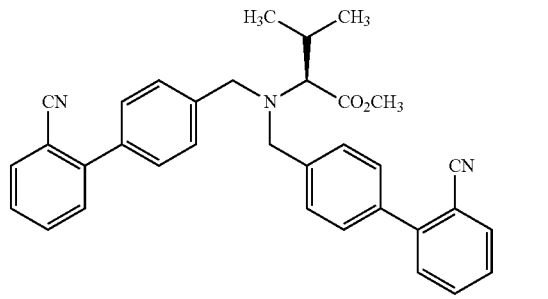

Formula Ia

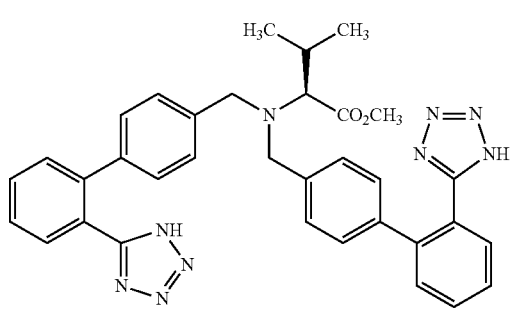

It was also observed with the prior-art processes, that the condensation of compound of formula (VI) with n-valeroyl chloride resulted about 2% unwanted alkene impurity of formula (VIIa) along with desired compound of formula (VII). This impurity in turn is carried forward in subsequent reaction steps and results in Valsartan (I) with the undesired impurity of formula (Ib). This results in the poor yield and quality of the Valsartan product and requires additional purification step.

Formula VIIa

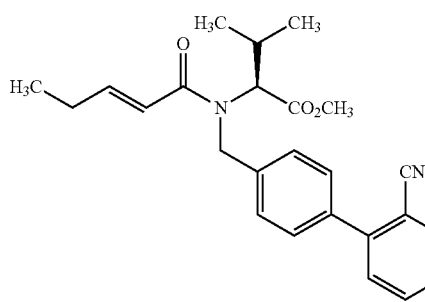

Formula Ib

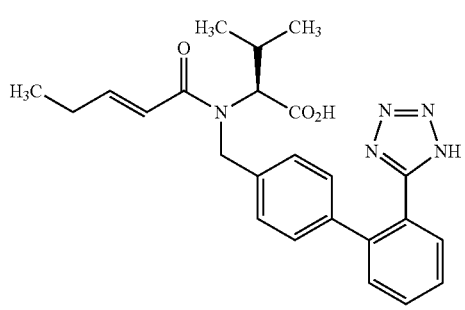

Further, it was observed that the formation of thermal degradation impurity of formula (VIIIa), which was formed during the conversion of compound of formula (VII) to compound of formula (VIIIb). This impurity in turn is carried forward in subsequent reaction steps and results in Valsartan (I) with the undesired impurity of formula (Ic). This results in the poor yield and quality of the Valsartan product and requires additional purification step.

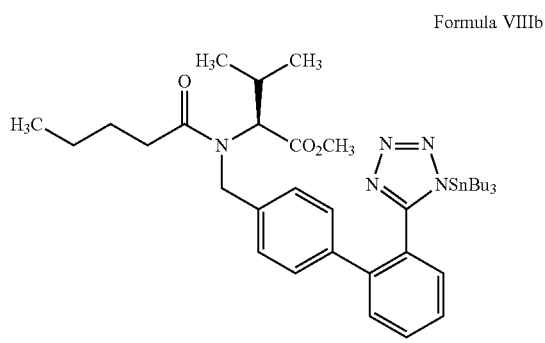

Hence, there is a need to have simple, easy to handle and cost effective process for the preparation of Valsartan and its intermediates with high chemical purity and optical purity.

The present invention is specifically directed towards the process for the preparation of intermediate compounds of formulae (VI), (VII) and (VIIIb), which are substantially free from their dimeric impurity of formula (VIa), alkene impurity of formula (VIIa) and thermal degradation impurity of formula (VIIIa) respectively.

The present invention also directed to a one-pot process for the preparation of pure Valsartan substantially free from impurities of formulae (Ia), (Ib), and (Ic).

OBJECTIVE OF INVENTION

The main objective of the present invention is to provide a simple and cost-effective process for the preparation of Valsartan of high purity on commercial scale.

SUMMARY OF THE INVENTION

The present invention relates to a process for the preparation of pure Valsartan substantially free from impurities of formulae (Ia), (Ib), and (Ic), which comprises:
(i) condensing 2-(4'-bromomethylphenyl)benzonitrile of formula (II), with L-valine methyl ester hydrochloride of formula (V), in the presence of a base in a solvent to produce N-[(2'-cyanobiphenyl-4-yl)methyl]-(L)-valine methyl ester of formula (VI), (ii) treating the compound (VI) of step (i) with acid followed by treating with base to produce pure compound (VI) substantially free from dimeric impurity of formula (VIa);
(iii) reacting the pure compound of formula (VI) with n-valeryl chloride in the presence of a base to produce pure N-valeryl-N-[(2'-cyanobiphenyl-4-yl)methyl]-(L)-valine methyl ester (VII) substantially free from alkene impurity of formula (VIIa);

Formula VII

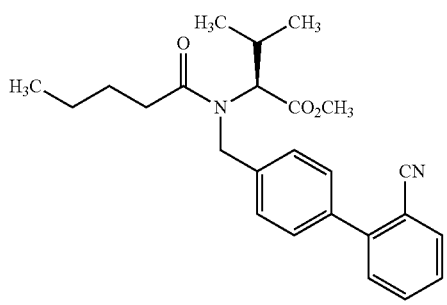

(iv) reacting the compound of formula (VII) with trialkyltin chloride and a metal azide in a solvent at a reflux temperature to produce N-(1-oxopentyl)-N-[[2'-(2-tributyltintetrazol-5-yl)-(1,1'-biphenyl)-4-yl]methyl]-(L)-valine methyl ester of formula (VIIIb) free from thermal degradation impurity (VIIIa);

Formula VIIIb

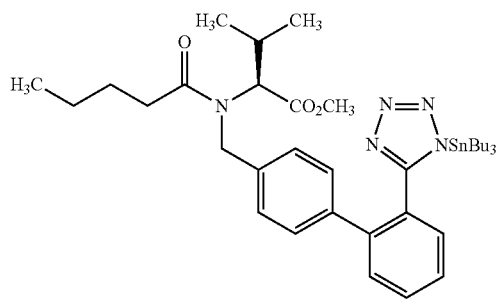

(v) hydrolyzing the compound of formula (VIIIb) in the presence of alkaline conditions to produce Valsartan (I).

In another embodiment, the present invention also provides one-pot process for the preparation of Valsartan (I) without isolating the intermediate compounds N-[(2'-cyanobiphenyl-4-yl)methyl]-(L)-valine methyl ester (VI), N-valeryl-N-[(2'-cyanobiphenyl-4-yl)methyl]-(L)-valine methyl ester (VII) and N-(1-oxopentyl)-N-[[2'-(2-tributyltintetrazol-5-yl)-(1,1'-biphenyl)-4-yl]methyl]-(L)-valine methyl ester (VIIIb).

In another embodiment, the present invention also provides a process for the preparation of pure Valsartan (I) substantially free from impurity of formula (Ia), which comprises:

(i) condensing 2-(4'-bromomethylphenyl)benzonitrile of formula (II),

Formula II

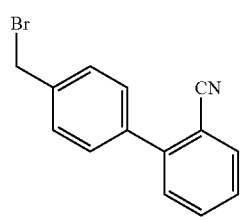

with L-valine methyl ester hydrochloride of formula (V),

Formula V

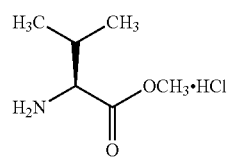

in the presence of a base in a solvent to produce N-[(2'-cyanobiphenyl-4-yl)methyl]-(L)-valine methyl ester of formula (VI);

Formula VI

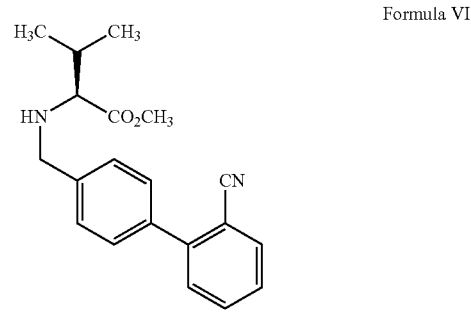 [SMILES: COC(=O)[C@@H](NCc1ccc(-c2ccccc2C#N)cc1)C(C)C]

(ii) treating the compound (VI) of step (i) with acid followed by treating with base to produce pure compound (VI) substantially free from dimeric impurity of formula (VIa);

(iii) converting the pure compound (VI) of step (ii) to produce Valsartan (I).

In another embodiment, the present invention also provides a process for the preparation of pure Valsartan (I) substantially free from impurity of formula (Ib):

which comprises, (i) reacting the compound of formula (VI) with n-valeryl chloride in the presence of a heterocyclic amine base selected from 2,6-lutidine, 2,4-lutidine, 2,3-lutidine, 3,4-lutidine, 2,5-lutidine, 3,5-lutidine in a solvent to produce pure N-valeryl-N-[(2'-cyanobiphenyl-4-yl)methyl]-(L)-valine methyl ester (VII) substantially free from alkene impurity of formula (VIIa);

Formula VII

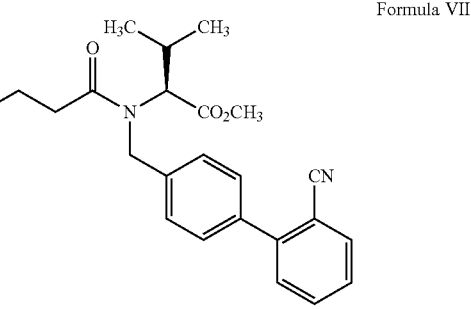

(ii) converting the pure compound (VII) of step (i) to produce Valsartan (I).

In another embodiment, the present invention also provides a process for the preparation of pure Valsartan (I) substantially free from impurity of formula (Ic):

which comprises, (i) Reacting the compound of formula (VII) with trialkyltin chloride and a metal azide in a solvent at a reflux temperature to produce N-(1-oxopentyl)-N-[[2'-(2-tributyltintetrazol-5-yl)-(1,1'-biphenyl)-4-yl]methyl]-(L)-valine methyl ester of formula (VIIIb) free from thermal degradation impurity (VIIIa);

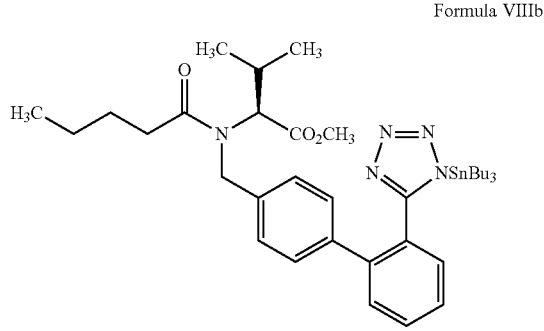

Formula VIIIb (ii) hydrolyzing the compound of formula (VIIIb) in the presence of alkaline conditions to produce Valsartan (I).

DETAILED DESCRIPTION OF THE INVENTION

The present invention relates to a process for the preparation of pure Valsartan substantially free from impurities of formulae (Ia), (Ib), and (Ic).

The process comprises, condensation of 4'-bromomethyl-2-cyanobiphenyl (II) with L-valine methyl ester hydrochloride (V) in the presence of a base selected from sodium carbonate, sodium bicarbonate, potassium carbonate in a solvent selected from ethers, esters, chlorinated solvents or mixtures thereof to produce N-[(2'-cyanobiphenyl-4-yl)methyl]-(L)-valine methyl ester (VI) containing about 5% of dimeric impurity of formula (VIa). The reaction is carried out at a temperature of about 30-80° C. for a period of about 20 to 30 hours.

After completion of reaction as ascertained by the known detection methods reported in the art such as HPLC, reaction mass is diluted with water and treated with an acid selected from hydrochloric acid, hydrobromic acid to a pH about 0.5 to 1, followed by separating the aqueous layer and extracting the product in to solvent selected from toluene, ethyl acetate, methylene chloride, acetic acid, formic acid, sulfuric acid by adjusting the pH about 7.5-9.0 with an aqueous base selected from sodium carbonate, sodium bicarbonate, potassium carbonate and washed with water followed by concentrated under reduced pressure and re dissolved in a solvent selected from toluene, ethyl acetate, methylene chloride to produce pure N-[(2'-cyanobiphenyl-4-yl)methyl]-(L)-valine methyl ester (VI) substantially free from dimeric impurity of formula (VIa).

Reacting pure N-[(2'-cyanobiphenyl-4-yl)methyl]-(L)-valine methyl ester (VI) with n-valeryl chloride in the presence of a heterocyclic amine base selected from 2,6-lutidine, 2,4-lutidine, 2,3-lutidine, 3,4-lutidine, 2,5-lutidine, 3,5-lutidine to produce pure N-valeryl-N-[(2'-cyanobiphenyl-4-yl)methyl]-(L)-valine methyl ester (VII) substantially free from alkene impurity of formula (VIIa).

The reaction temperature for the above reaction is from about 0° C. to about 50° C. The sufficient period of time necessary for obtaining compound (VII) will depend on the parameters of the reaction. Preferably, maintaining the reaction mixture for about 1 to about 5 hours.

After completion of reaction as ascertained by the known detection methods reported in the art such as HPLC, reaction mass is diluted with water and separated the organic layer and washed the organic layer with aqueous base selected from sodium carbonate, sodium bicarbonate, potassium carbonate and washed with water followed by concentrated under reduced pressure and re dissolved in a solvent selected from toluene, ethyl acetate, methylene chloride to produce pure N-valeryl-N-[(2'-cyanobiphenyl-4-yl)methyl]-(L)-valine methyl ester (VII) substantially free from alkene impurity of formula (VIIa).

The organic layer containing N-valeryl-N-[(2'-cyanobiphenyl-4-yl)methyl]-(L)-valine methyl ester (VII) is treated with trialkyltin chloride and a metal azide in a solvent at a reflux temperature to produce N-(1-oxopentyl)-n-[[2'-(2-tributyltintetrazol-5-yl)-(1,1'-biphenyl)-4-yl]methyl]-(L)-valine methyl ester (VIIIb) substantially free from thermal degradation impurity (VIIIa).

The trialkyl tin chloride used is selected from trimethyltin chloride, triethyltin chloride, tributyltin chloride and the like. The metal azide is selected from inorganic azide like sodium, potassium or lithium azide.

The solvent used in the reaction is selected from aromatic hydrocarbon selected from toluene, xylene. The reaction is carried out at a temperature of about 80 to 130° C. The sufficient period of time necessary for obtaining compound (VIIIb) will depend on the parameters of the reaction. Preferably, maintaining the reaction mixture for about 40 to about 60 hours.

After completion of reaction as ascertained by the known detection methods reported in the art such as HPLC, reaction mass is used as such in the next step or by isolating compound (VIIIb) by conventional methods such as extracting with a solvent, followed by separating the layers and concentrated. On the other hand it can also by isolated by crystallizing from the reaction mass by cooling the reaction mass or by adding anti-solvent.

The reaction mass containing N-(1-oxopentyl)-n-[[2'-(2-tributyltintetrazol-5-yl)-(1,1'-biphenyl)-4-yl]methyl]-(L)-valine methyl ester (VIIIb) is treated with aqueous base selected from lithium hydroxide, sodium hydroxide, potassium hydroxide, cesium hydroxide, barium hydroxide to produce Valsartan (I). After completion of reaction as ascertained by the known detection methods reported in the art such as HPLC, the aqueous layer was separated and extracting the reaction mass with a solvent, followed by adjusting the pH to about 2.5 to about 4.0 with an acid. The organic layer is separated and washed with water and concentrated to residue.

The reaction temperature for the above reaction is from about 15° C. to about 40° C. The solvent used for the extraction is selected from methylene chloride, ethyl acetate, chloroform, methyl tertiary butyl ether, toluene or mixtures thereof. The acid used to adjust the pH is selected from hydrochloric acid, hydrobromic acid, sulfuric acid, acetic acid.

In another embodiment, the present invention also relates to one-pot process for the preparation of Valsartan (I) without isolating the intermediate compounds N-[(2'-cyanobiphenyl-4-yl)methyl]-(L)-valine methyl ester (VI), N-valeryl-N-[(2'-cyanobiphenyl-4-yl)methyl]-(L)-valine methyl ester (VII) and N-(1-oxopentyl)-N-[[2'-(2-tributyltintetrazol-5-yl)-(1,1'-biphenyl)-4-yl]methyl]-(L)-valine methyl ester (VIIIb).

Valsartan (I) obtained by the above methods is further purified by known methods, for example by dissolving in a solvent selected from methanol, ethanol, isopropanol, methylene chloride, tetrahydrofuran, ethyl acetate or mixtures thereof and precipitating pure Valsartan (I) by cooling the solution to about 0-30° C., or by adding an anti solvent selected from cyclohexane, n-hexane, heptane etc.

EXAMPLES

Example 1

Stage-1

Preparation of N-[(2'-cyanobiphenyl-4-yl)methyl]-(L)-valine methyl ester (VI)

4'-Bromomethyl-2-cyanobiphenyl (75 g, 0.2757 moles) was added to a mixture of potassium carbonate (95.12 g), DM water (225 ml), ethyl acetate (450 ml) and L-valine methyl ester hydrochloride (55.45 g, 0.330 moles) at 20-30° C. The reaction mixture was heated to 40-50° C. and stirred for 25 h. After completion of the reaction, the ethyl acetate layer was separated at 20-30° C., added DM water (375 ml) and adjusted the pH to 0.8-1.0 with dilute hydrochloric acid at 20-30° C. The aqueous layer was separated and extracted the product in to toluene (430 ml) by adjusting the pH to 8.0-8.5 with 20% w/w aqueous sodium carbonate solution. The toluene layer was washed with DM water (225 ml), concentrated under reduced pressure and dissolved in toluene (450 ml)

Chromatographic Purity: 99.86% (HPLC)
Formula VIa Impurity: 0.08%

Stage-2

Preparation of N-[(2'-cyanobiphenyl-4-yl)methyl]-N-valeryl-(L)-valine methyl ester (VII)

The toluene solution obtained in stage-1 was cooled to 5-10° C. and 2,6-lutidine (32.45 g, 0.303 moles) followed by valeryl chloride (36.54 g, 0.303 moles) were added at 5-10° C. in 1 h. After addition, the reaction mass temperature was raised to 25-30° C. and stirred for 1 h. DM water (225 ml) was added to the reaction at 20-30° C., separated the organic layer and washed with 5% w/w aqueous sodium carbonate solution (75 ml)

Chromatographic Purity: 99.69% (HPLC)
Formula VIIIa Impurity: Not detected

Stage-3

Preparation of N-(1-oxopentyl)-N-[[2'-(2-tributyltintetrazol-5-yl)-(1,1'-biphenyl)-4-yl]methyl]-(L)-valine methyl ester (VIIIb)

Tri-n-butyltin chloride (242.32 g, 0.744 moles) and sodium azide (50.18 g, 0.772 moles) were added to the organic layer containing N-(1-oxopentyl)-N-[[2'-(2-tributyltintetrazol-5-yl)-(1,1'-biphenyl)-4-yl]methyl]-(L)-valine methyl ester (VIIIb), obtained in stage-2, maintained at reflux temperature for 50 h and cooled to 20-30° C.

Chromatographic Purity: 94.40% (HPLC)
Formula VIIIa Impurity: 0.13%

Stage-4

Preparation of N-(1-oxopentyl)-N-[[2'-(1H-tetrazol-5-yl)-(1,1'-biphenyl)-4-yl]methyl]-(L)-valine (I) (Valsartan)

7.5% w/w aqueous sodium hydroxide solution (882.2 g, 1.654 moles) was added to the reaction mass obtained in stage-3, at 20-30° C. and stirred for 12 h. After completion of the hydrolysis, the aqueous layer was separated and washed with toluene (150 ml) Ethyl acetate (750 ml) was added to the aqueous layer, and adjusted the pH to 1.0-2.5 with dilute hydrochloric acid. The organic layer was separated, washed with DM water (225 ml) and concentrated under reduced pressure.

Chromatographic Purity: 99.54% (HPLC)
Formula Ia Impurity: Not detected
Formula Ib Impurity: Not detected
Formula Ic Impurity: 0.13%

Stage-5

Crystallization of Valsartan (I)

The concentrated mass obtained in Stage-4, was dissolved in ethyl acetate (450 ml), treated with carbon enoanticromos (7.5 g) at 50-55° C. and filtered. The filtrate was cooled to 0-5° C., isolated the product and dried at 55-60° C.

Yield: 67.5 g; 56.25%
Chromatographic Purity: 99.9% (HPLC)
Formula Ia Impurity: Not detected
Formula Ib Impurity: Not detected
Formula Ic Impurity: Not detected

Example-2

Stage-1

Preparation of N-[(2'-cyanobiphenyl-4-yl)methyl]-(L)-valine methyl ester (VI)

4'-Bromomethyl-2-cyanobiphenyl (15 g, 0.0551 moles) was added to a mixture of potassium carbonate (19.05 g), DM water (45 ml), ethyl acetate (60 ml) and L-valine methyl ester hydrochloride (11.09 g, 0.066 moles) at 20-30° C. The reaction mixture was heated to 40-50° C. and stirred for 25 h. After completion of the reaction, the ethyl acetate layer was separated at 20-30° C., concentrated under reduced pressure and dissolved in o-xylene (90 ml)

Chromatographic Purity: 94.68% (HPLC)
Formula VIa Impurity: 1.55%

Stage-2

Preparation of N-[(2'-cyanobiphenyl-4-yl)methyl]-N-valeryl-(L)-valine methyl ester (VII)

N,N-Diisopropylethylamine (12 g, 0.0937 moles) followed by valeryl chloride (11.3 g, 0.0937 moles) were added to the o-xylene solution obtained in stage-2, at 20-25° C. and stirred for 3 h. DM water (75 ml) was added to the reaction at 20-30° C., and separated the organic layer and washed with 5% w/w aqueous sodium carbonate solution (15 ml)

Chromatographic Purity: 92.92% (HPLC)
Formula VIIa Impurity: 0.17%

Stage-3

Preparation of N-(1-oxopentyl)-N-[[2'-(2-tributyltintetrazol-5-yl)-(1,1'-biphenyl)-4-yl]methyl]-(L)-valine methyl ester (VIIIb)

Tri-n-butyltin chloride (62.8 g, 0.1928 moles) and sodium azide (13.28 g, 0.2040 moles) were added to the organic layer, obtained in stage and maintained the reaction at reflux temperature for 50 h and cooled to 20-30° C.

Chromatographic Purity: 93.01% (HPLC)
Formula VIIIa Impurity: 0.17%

Stage-4

Preparation of N-(1-oxopentyl)-N-[[2'-(1H-tetrazol-5-yl)-(1,1'-biphenyl)-4-yl]methyl]-(L)-valine (I) (Valsartan)

6% w/w aqueous sodium hydroxide solution (220.2 g, 0.3308 moles) was added to the reaction mass obtained in step-3, at 20-30° C. and stirred for 15 h. After completion of the hydrolysis, the aqueous layer was separated and washed with o-xylene (45 ml) Ethyl acetate (150 ml) was added to the aqueous layer, and adjusted the pH to 3.0 with dilute hydrochloric acid. The organic layer was separated and treated with 10% w/w aqueous sodium carbonate solution (292 g) at 20-30° C. The aqueous layer was separated, pH of the aqueous layer was adjusted to 6.0-6.5 with dilute hydrochloric acid and washed with methylene chloride (2×45 ml) at 20-30° C. Ethyl acetate (150 ml) was added to the aqueous layer and adjusted the pH to 2.5-3.0 with dilute hydrochloric acid at 20-30° C. The ethyl acetate layer was separated, washed with DM water (75 ml) and concentrated under reduced pressure.

Chromatographic Purity: 96.50% (HPLC)
Formula Ia Impurity: 1.47%
Formula Ib Impurity: 0.03%
Formula Ic Impurity: 0.25%

Stage-5

Crystallization of Valsartan (I)

The concentrated mass obtained in Example-2 d, was dissolved in ethyl acetate (105 ml), treated with carbon enoanticromos (0.75 g) at 50-55° C. and filtered. The filtrate was cooled to 0-5° C., isolated the product and dried at 55-60° C.

Yield: 13.9 g; 57.91%
Chromatographic Purity: 99.53% (HPLC)
Formula Ia Impurity: 0.11%
Formula Ib Impurity: 0.03%
Formula Ic Impurity: 0.05%

We claim:

1. A process for the preparation of Valsartan of formula (I) substantially free from impurities of formulae (Ia), (Ib), and (Ic),

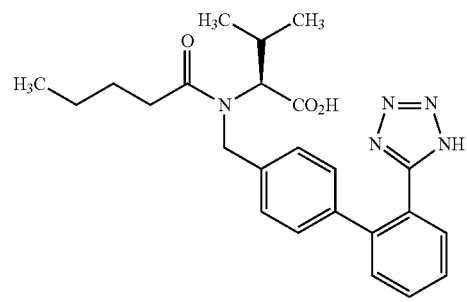

Formula I

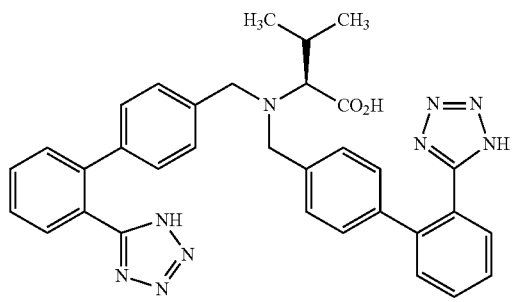

Formula Ia

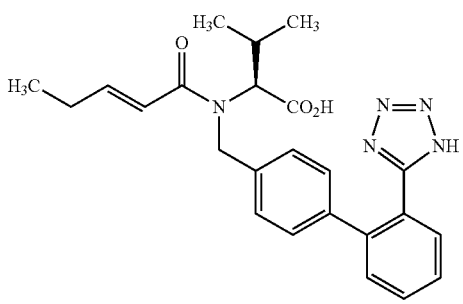

Formula Ib

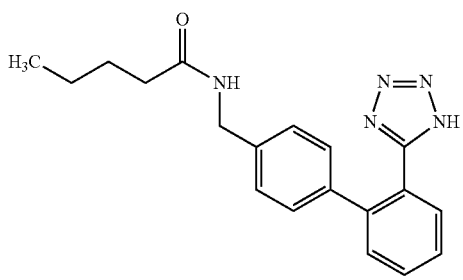

Formula Ic which comprises:

(i) condensing 2-(4'-bromomethylphenyl)benzonitrile of formula (II),

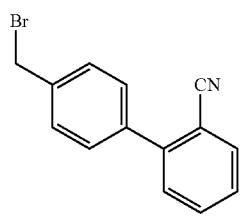

Formula II with L-valine methyl ester hydrochloride of formula (V),

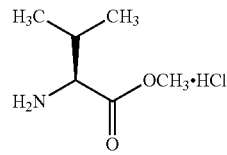

Formula V in the presence of a base in a solvent to produce N-[(2'-cyanobiphenyl-4-yl)methyl]-(L)-valine methyl ester of formula (VI);

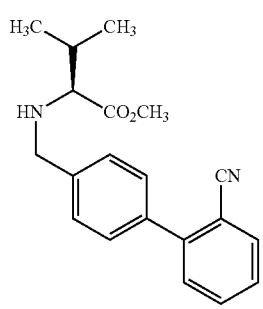

Formula VI (ii) treating the compound (VI) of step (i) with acid followed by treating with base to produce pure compound (VI) substantially free from dimeric impurity of formula (VIa);

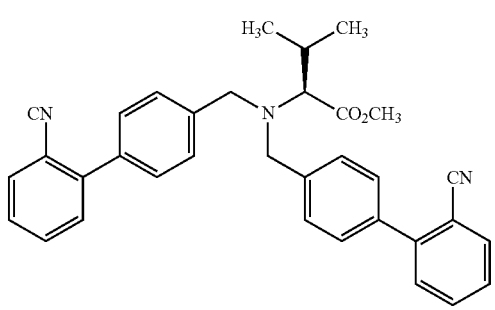

Formula VIa (iii) reacting the pure compound of formula (VI) with n-valeryl chloride in the presence of a base to produce pure N-valeryl-N-[(2'-cyanobiphenyl-4-yl)methyl]-(L)-valine methyl ester (VII) substantially free from alkene impurity of formula (VIIa);

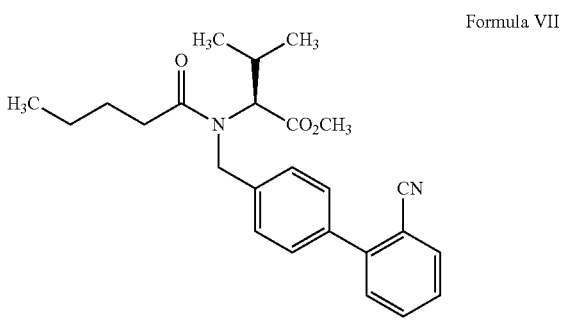 [SMILES: CCCCC(=O)N(Cc1ccc(-c2ccccc2C#N)cc1)[C@H](C(=O)OC)C(C)C]

Formula VII

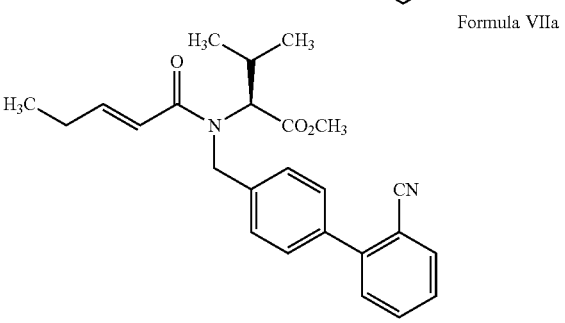

Formula VIIa (iv) reacting the compound of formula (VII) with trialkyl-tin chloride and a metal azide in a solvent at a reflux temperature to produce N-(1-oxopentyl)-N-[[2'-(2-tributyltintetrazol-5-yl)-(1,1'-biphenyl)-4-yl]methyl]-(L)-valine methyl ester of formula (VIIIb) free from thermal degradation impurity (VIIIa);

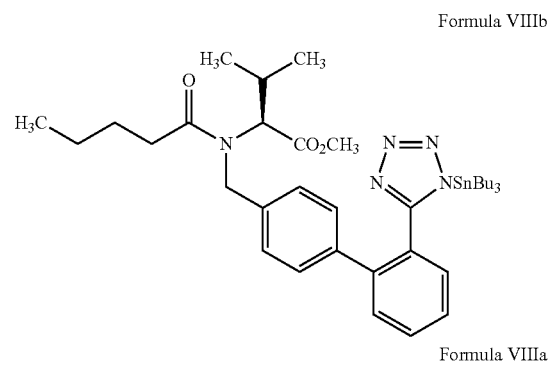

Formula VIIIb

Formula VIIIa (v) hydrolyzing the compound of formula (VIIIb) in the presence of alkaline conditions to produce Valsartan (I).

2. The process according to claim 1, wherein the above process is carried out without isolating the intermediate compounds N-[(2'-cyanobiphenyl-4-yl)methyl]-(L)-valine methyl ester (VI), N-valeryl-N-[(2'-cyanobiphenyl-4-yl)methyl]-(L)-valine methyl ester (VII) and N-(1-oxopentyl)-N-[[2'-(2-tributyltintetrazol-5-yl)-(1,1'-biphenyl)-4-yl]methyl]-(L)-valine methyl ester (VIIIb).

3. The process according to claim 1, wherein the base used in step-(i) is sodium carbonate, sodium bicarbonate or potassium carbonate.

4. The process according to claim 1, wherein the acid used in step-(ii) is hydrochloric acid or hydrobromic acid.

5. The process according to claim 1, wherein the base used in step-(iii) is 2,6-lutidine, 2,4-lutidine, 2,3-lutidine, 3,4-lutidine, 2,5-lutidine or 3,5-lutidine.

6. The process according to claim 1, wherein the trialkyl tin chloride used in step-(iv) is trimethyltin chloride, triethyltin chloride or tributyltin chloride.

7. The process according to claim 1, wherein the alkaline solution used in step-(v) comprises lithium hydroxide, sodium hydroxide, potassium hydroxide, cesium hydroxide, barium hydroxide or mixtures thereof.

8. The process according to claim 1, wherein the solvent used in step-(i) is ether, ester, chlorinated solvent or mixtures thereof.

9. The process according to claim 1, wherein the base used in step-(ii) is sodium carbonate, sodium bicarbonate or potassium carbonate.

10. The process according to claim 1, wherein the metal azide used in step-(iv) is sodium azide, potassium azide or lithium azide.

11. A process for the preparation of pure Valsartan (I) substantially free from impurity of formula (Ia);

Formula I

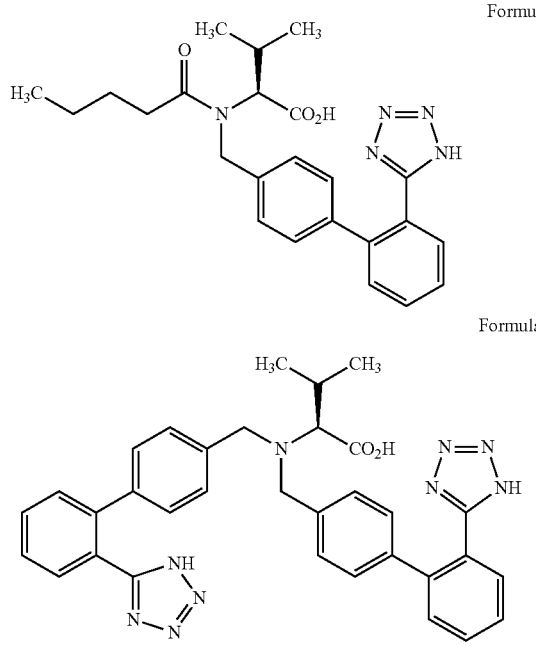

Formula Ia which comprises,
(i) condensing 2-(4'-bromomethylphenyl)benzonitrile of formula (II)

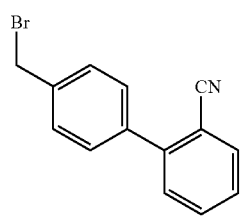

Formula II with L-valine methyl ester hydrochloride of formula (V);

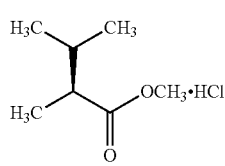

Formula V in the presence of a base in a solvent to produce N-[(2'-cyanobiphenyl-4-yl)methyl]-(L)-valine methyl ester of formula (VI);

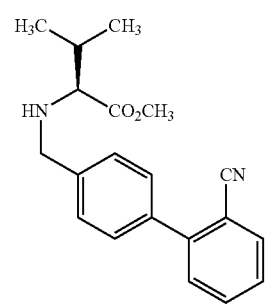

Formula VI (ii) treating the compound (VI) of step (i) with an acid followed by treating with a base to produce pure compound (VI) substantially free from dimeric impurity of formula (VIa);

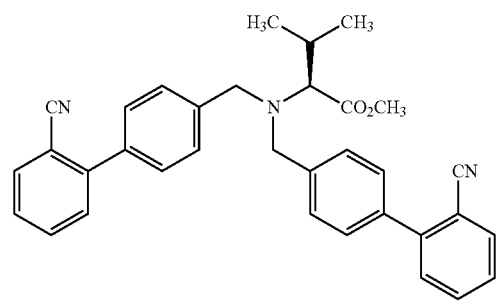

Formula VIa (iii) converting the pure compound (VI) of step (ii) to produce Valsartan (I).

12. A process for the preparation of pure Valsartan (I) substantially free from impurity of formula (Ib);

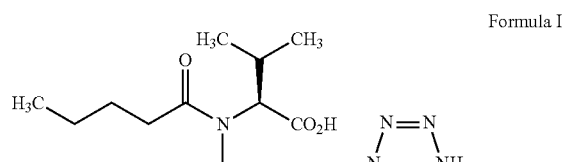

Formula I

Formula Ib which comprises,
(i) reacting the compound of formula (VI);

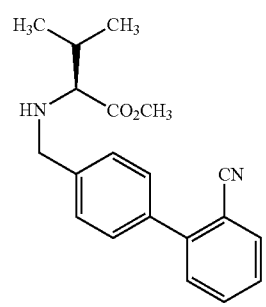

Formula VI with n-valeryl chloride in the presence of a heterocyclic amine base to produce pure N-valeryl-N-[(2'-cyano-biphenyl-4-yl)methyl]-(L)-valine methyl ester (VII)

substantially free from alkene impurity of formula (VIIa);

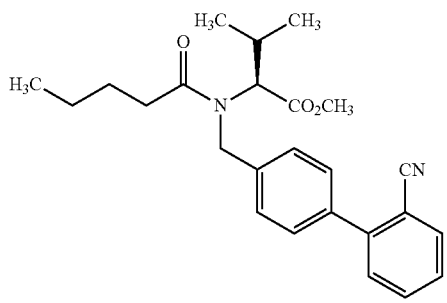
Formula VII

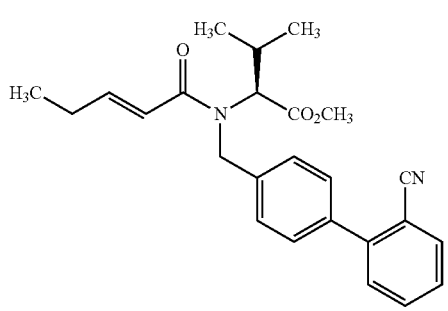
Formula VIIa wherein, the heterocyclic amine base is 2,6-lutidine, 2,4-lutidine, 2,3-lutidine, 3,4-lutidine, 2,5-lutidine or 3,5-lutidine,
(ii) converting the pure compound (VII) of step (i) to produce Valsartan (I).

13. A process for the preparation of pure Valsartan (I) substantially free from impurity of formula (Ic);

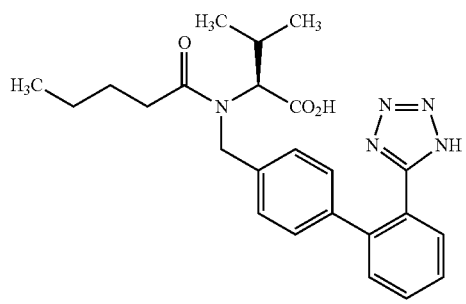
Formula I

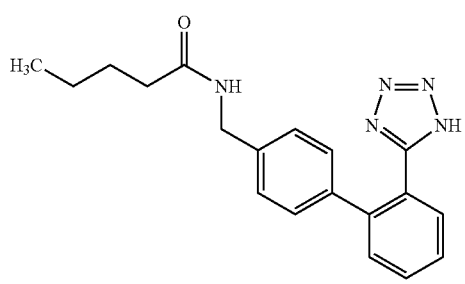
Formula Ic which comprises,
(i) reacting the compound of formula (VII);

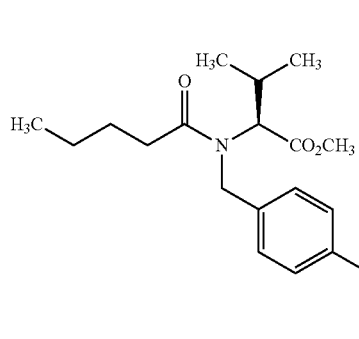
Formula VII with trialkyltin chloride and a metal azide in a solvent at reflux temperature to produce N-(1-oxopentyl)-N-[[2'-(2-tributyltintetrazol-5-yl)-(1,1'-biphenyl)-4-yl]methyl]-(L)-valine methyl ester of formula (VIIIb) free from thermal degradation impurity (VIIIa);

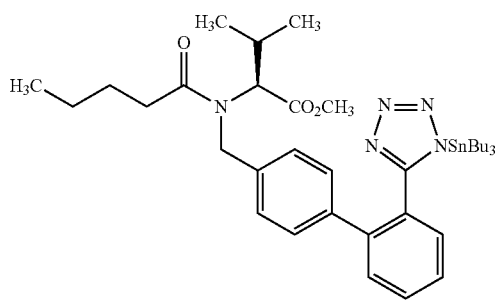
Formula VIIIb

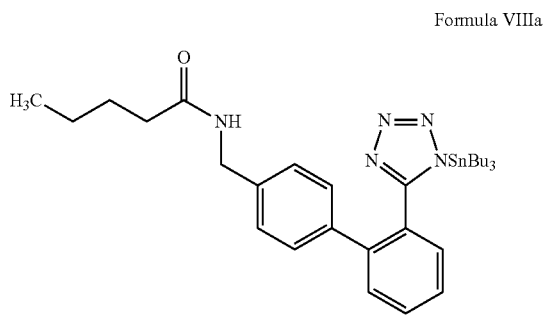
Formula VIIIa (ii) hydrolyzing the compound of formula (VIIIb) in the presence of alkaline conditions to produce Valsartan (I).

* * * * *